(12) United States Patent
Graze, Jr.

(10) Patent No.: US 8,505,395 B2
(45) Date of Patent: Aug. 13, 2013

(54) DILUTION SYSTEM TEST APPARATUS WITH ADDED CAPABILITY AND METHOD OF OPERATING SAME

(75) Inventor: Russell R. Graze, Jr., Dunlap, IL (US)

(73) Assignee: Caterpillar Inc., Peoria, IL (US)

( * ) Notice: Subject to any disclaimer, the term of this patent is extended or adjusted under 35 U.S.C. 154(b) by 803 days.

(21) Appl. No.: 12/546,744

(22) Filed: Aug. 25, 2009

(65) Prior Publication Data

US 2011/0048105 A1 Mar. 3, 2011

(51) Int. Cl.
*G01N 1/00* (2006.01)

(52) U.S. Cl.
USPC ..................................... 73/863.51; 73/863.71

(58) Field of Classification Search
USPC ............... 73/863.51, 863.53, 863.58, 863.71, 73/863.91
See application file for complete search history.

(56) References Cited

U.S. PATENT DOCUMENTS

| | | | | |
|---|---|---|---|---|
| 3,406,562 A | * | 10/1968 | Perna, Jr. et al. | 73/23.31 |
| 4,633,706 A | * | 1/1987 | Ito et al. | 73/23.33 |
| 4,747,297 A | * | 5/1988 | Okayama et al. | 73/23.33 |
| 4,814,143 A | * | 3/1989 | Kojima et al. | 422/83 |
| 4,916,384 A | * | 4/1990 | Ishida | 324/71.4 |
| 5,052,425 A | * | 10/1991 | Hohenberg et al. | 137/1 |
| 5,410,907 A | * | 5/1995 | Strom et al. | 73/23.31 |
| 5,469,731 A | * | 11/1995 | Decker et al. | 73/23.31 |
| 5,486,220 A | * | 1/1996 | Honda et al. | 55/487 |
| 5,621,166 A | * | 4/1997 | Butler | 73/114.71 |
| 6,058,789 A | * | 5/2000 | Kohsaka et al. | 73/863.11 |
| 6,134,942 A | * | 10/2000 | Pasquereau et al. | 73/23.31 |
| 6,178,830 B1 | * | 1/2001 | Freud | 73/863.51 |
| 6,481,299 B2 | * | 11/2002 | Silvis et al. | 73/863.81 |
| 6,615,677 B2 | | 9/2003 | Dickson et al. | |
| 6,725,653 B2 | * | 4/2004 | Brown et al. | 60/297 |
| 6,823,268 B2 | * | 11/2004 | Silvis et al. | 702/30 |
| 6,823,748 B2 | * | 11/2004 | Silvis et al. | 73/863.03 |
| 7,059,205 B1 | * | 6/2006 | Weaver | 73/863.03 |
| 7,191,671 B2 | * | 3/2007 | Kreft | 73/863.81 |
| 7,201,071 B2 | | 4/2007 | Wei et al. | |
| 7,299,690 B2 | | 11/2007 | Graze, Jr. | |
| 7,389,703 B2 | | 6/2008 | Wei et al. | |
| 7,404,340 B2 | | 7/2008 | Dickson et al. | |
| 7,406,885 B2 | * | 8/2008 | Graze, Jr. | 73/863.01 |
| 7,434,449 B2 | * | 10/2008 | Kusaka et al. | 73/23.31 |
| 2002/0020232 A1 | * | 2/2002 | Yamagishi et al. | 73/863.11 |
| 2004/0074319 A1 | * | 4/2004 | Silvis et al. | 73/864.73 |
| 2005/0109128 A1 | * | 5/2005 | Pasquereau et al. | 73/863.21 |
| 2008/0087107 A1 | | 4/2008 | Silvis et al. | |

FOREIGN PATENT DOCUMENTS

| | | |
|---|---|---|
| EP | 0 471 174 B1 | 2/1992 |
| EP | 0 501 242 B1 | 9/1992 |
| JP | 01031032 A * | 2/1989 |
| JP | 08254487 A * | 10/1996 |

(Continued)

*Primary Examiner* — David Rogers
(74) *Attorney, Agent, or Firm* — Liell & McNeil

(57) ABSTRACT

A partial dilution exhaust sampling system has an expanded ability to simultaneously perform two different evaluations on exhaust from a power source. Beyond testing for particulate matter production, the system may simultaneously evaluate exhaust for undesirable gaseous emissions such as NOx and carbon dioxide and/or concurrently evaluate particle size and distribution in the exhaust sample. After extracting sample flow from the exhaust stream of the power source and adding diluent to the sample flow, the diluted sample flow is divided into a first portion flow and a second portion flow. Depending upon whether the additional exhaust evaluation device is in parallel with the particulate measurement gravimetric filter or in series with the filter, a dilution flow actuator and/or an exit actuator may be adjusted to account for a fraction of diluted sample flow directed to the auxiliary exhaust evaluation device.

17 Claims, 1 Drawing Sheet

(56) References Cited

FOREIGN PATENT DOCUMENTS

| | | | | |
|---|---|---|---|---|
| JP | 08278237 | A | * | 10/1996 |
| JP | 10104134 | | | 4/1998 |
| JP | 2000028498 | | | 1/2000 |
| JP | 2000028499 | A | * | 1/2000 |
| JP | 2000292322 | A | * | 10/2000 |
| JP | 2000329661 | A | * | 11/2000 |
| JP | 2008164413 | | | 7/2008 |

* cited by examiner

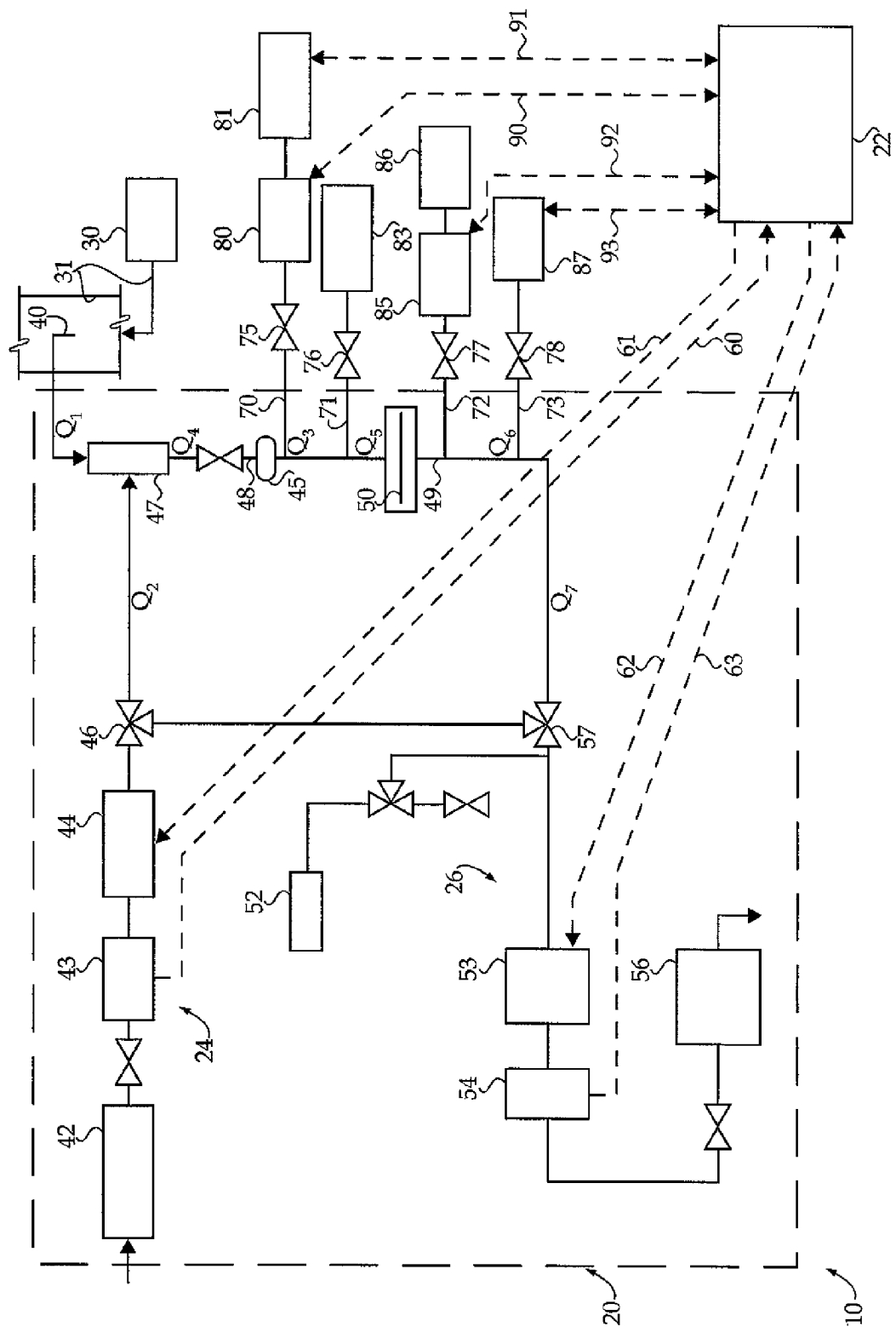

DILUTION SYSTEM TEST APPARATUS WITH ADDED CAPABILITY AND METHOD OF OPERATING SAME

TECHNICAL FIELD

The present disclosure relates generally to a proportional exhaust sampling system, and more particularly to a strategy for performing at least two simultaneous exhaust evaluation tests, especially during transient operating conditions of a power source being tested.

BACKGROUND

Exhaust emissions from motorized on-highway machines are regulated by the relevant government agencies and must not exceed certain contaminant levels. For example, some government regulations place limits on the amount, and maybe sizing, of particulate matter that may be emitted by diesel truck engines. Particulate matter may include, for example, carbon particulate, unburned hydrocarbons, and sulfates. Additional regulations may specify acceptable levels of gaseous emissions (e.g., NOx, CO) that may be part of the exhaust gas stream from the engine. Early regulations primarily addressed undesirable emission levels when the engine was operating in a relatively steady state condition. More recent regulations have been promulgated to regulate undesirable emissions when the engine is undergoing a transient condition, such as accelerating from one speed and load condition to another speed and load condition to another speed and load.

Due to these regulations, equipment has been developed to test and analyze machine engines and/or power sources for conformance with governmental standards. In particular, partial flow exhaust gas sampling systems have been developed in an effort to certify such power sources as being in compliance with government emissions regulations with regard to particulate matter. Generally, these systems operate by extracting a small portion of a power source's exhaust flow via a test probe located in the exhaust stack. A regulated flow of filtered ambient air is then mixed with the extracted portion, and the combined flow is directed to a filter configured to trap the particulate matter contained within the combined flow. The power source may then be evaluated based on the quantity of particulate matter trapped by the filter during a particular test cycle. Examples of such particulate sampling systems and methods that have performed well in recent years are shown and described in co-owned U.S. Pat. Nos. 6,615,677, 7,299,690, 7,404,340, 7,406,885 et al.

While these systems have shown the ability to perform well with regard to particulate matter assessments, there is a growing need to certify engines with regard to other undesirable emissions, including but not limited to particulate size and undesirable gaseous emissions including NOx and carbon monoxide. The alternative to partial flow systems might be a full dilution tunnel. However, these systems are extremely expensive and do not have the capability of testing a broad range of sizes of different diesel engines, and in fact do not have the capacity for some of the relatively large diesel engines that appear in some machines of the type manufactured by Caterpillar Inc. of Peoria Ill. Full dilution systems also face problems when attempting to perform simultaneous pre and post-after treatment sampling for system effectiveness studies, as the full-flow design of these systems makes such sampling physically impossible.

One potential solution to the problem of simultaneously evaluating exhaust emissions with two or more testing procedures could involve the usage of two or more partial flow dilution systems operating in parallel in one test cell. While such a solution may at first appear to be viable, the real estate available in a typical test cell may not allow for the associated hardware and computing equipment necessary to effectively operate two or more parallely arranged partial dilution sampling systems. On the other hand, incorporating an additional testing evaluation system, in addition to particulate matter weight systems typically associated with partial flow dilution systems, can also be problematic. In other words, the integrity of the particulate matter assessment relies heavily upon accurate measurement and control of exhaust sampling flow rates, residence time, dilution flow rates, flow velocity at the filter face, as well as assumptions associated with conservation of matter.

The systems and methods of the present disclosure are directed to overcome one or more of the problems set forth above.

SUMMARY OF THE DISCLOSURE

In one aspect, a method of operating a dilution system includes extracting a sample flow from an exhaust stream of a power source. Diluent is added to the sample flow to produce a diluted sample flow. The diluted sample flow is divided into a first portion flow that is directed to a first exhaust evaluation device, and a second portion flow that is directed to a second exhaust evaluation device.

In another aspect, a test probe is sized for opening into an exhaust line for receiving exhaust sample flow originating from a power source. A dilution device with a dilution flow actuator is included to add diluent to the sample flow to produce a diluted sample flow. A first exhaust evaluation device is fluidly positioned to receive a first portion of the diluted sample flow. A second exhaust evaluation device is fluidly positioned to receive a second portion of the diluted sample flow. An exit device, which includes a vacuum pump and an exit flow actuator, is fluidly positioned to receive at least part of the diluted sample flow.

In still another aspect, a first exhaust evaluation device includes a particulate measurement gravimetric filter fluidly positioned to receive a first portion of the diluted sample flow. The second exhaust evaluation device is one of a particle sizer, a particle counter, a soot sizer, a soot counter, a specialized gravimetric filter, a polyurethane foam cartridge, a gaseous emissions analyzer, or maybe a bag storage unit. The second exhaust evaluation device is fluidly positioned to receive a second portion of the diluted sample flow.

BRIEF DESCRIPTION OF THE DRAWING

FIG. 1 is a schematic view of a test apparatus according to one embodiment of the present disclosure.

DETAILED DESCRIPTION

Referring to FIG. 1, a test apparatus 10 includes a dilution system 20 situated for receiving combustion exhaust for testing from a power source 30, which may take the form of an internal combustion engine. The portion of the dilution system 20 enclosed by the dashed line is substantially identical to the well known dilution systems taught in the art, including the patent references identified in the background. Thus, much of the detail regarding the various apparatus, fluid connections, electrical connections and other features are omitted in FIG. 1 for the sake of clarity in describing the subject matter of the present disclosure. However, these various details are well known and described in numerous publications. As in the prior art, an exhaust stream from power source 30 travels through an exhaust line 31. A portion of that exhaust is captured by a test probe 40 that opens into the exhaust line. In other words, test probe 40 operates for receiving exhaust sample flow originating from power source 30.

As with prior art systems, a dilution device 24 provides a metered flow of filtered air for mixing with the sample flow in a dilution tunnel 47 and a residence chamber 45. This diluted sample flow is directed to a particulate measurement gravimetric filter 50, and thereafter an exit device 26, which includes a vacuum pump 56 that vents the remnants of the diluted sample flow to atmosphere in a conventional manner. The test apparatus 10 is controlled by an electronic controller 22, but only the control and communication lines relative to the present disclosure are shown. In particular, the overall flow rate through dilution system 20 is controlled by an exit flow actuator 53 that receives control commands from electronic controller 22 via communication line 62. The exit flow actuator 53 may be continuously adjusted based upon mass flow rate information provided to electronic controller 22 by exit flow meter 54 via communication line 63. The dilution ratio is controlled by electronic controller 22 via a diluent flow actuator 44 that receives commands via communication line 61. These commands may be based upon mass flow rate information provided by diluent flow meter 43 to electronic controller 22 via communication line 60. Like prior art systems, dilution system 20 includes a diluent treatment assembly 42 for filtering and cooling ambient air prior to being supplied to dilution device 24. In addition, system 20 includes valves 46 and 57, as well as a mass flow meter 52 and various other features known in the art and operated in a manner consistent with the descriptions contained in the previously identified references. Thus, prior art dilution systems typically include a single exhaust evaluation device, namely a particulate gravimetric filter 50, that permits a user to accurately assess the mass of particulate matter produced by a power source 30 during a test interval.

Test apparatus 10 and dilution system 20 differ from the prior art by the ability to perform some other exhaust evaluation function simultaneously with the collection of particles by the particulate filter 50. This is accomplished with appropriate additional plumbing to divide a diluted sample flow and direct different portions for collection and/or testing by different exhaust evaluation devices. The auxiliary exhaust evaluation feature may be accomplished by the inclusion of one or more branch passages 70, 71, 72 or 73 that receive a portion of the diluted sample flow from fluid conduits 48 and/or 49 that are located upstream and downstream from a particulate measurement gravimetric filter 50. In the illustrated embodiment, four auxiliary evaluation devices 81, 83, 86 and 87 are shown illustrated. However, if any of the conduits 70-73 were not being utilized during a particular testing procedure of power source 30, a respective isolation valve 75, 76, 77 or 78 allows for closure of the respective conduits 70-73, as illustrated. Depending upon the nature of the auxiliary exhaust evaluation device, a dedicated mass flow controller may be included to precisely meter (control and/or measure) diluted sample flow to the relevant exhaust evaluation device. Conversely, some exhaust evaluation devices may not include as a portion of their hardware a dedicated mass flow controller for precisely metering a desired mass flow rate of diluted sample flow to the relevant testing apparatus within the device. For instance, exhaust evaluation device 81 receives a metered precise mass flow rate of diluted sample flow via a mass flow controller 80 that communicates mass flow rate information, and receives mass flow control commands from, electronic controller 22 via communication line 90. On the other hand, exhaust evaluation device 83 may have some other internal means known in the art for precisely controlling mass flow rate equipment associated with exhaust evaluation device 83. In addition, depending upon the circumstances, the exhaust evaluation device itself may or may not communicate directly with electronic controller 22. In the illustrated embodiment, exhaust evaluation device 81 maintains a communication link with electronic controller 22 via communication line 91 whereas exhaust evaluation device 83 performs its function without the necessity of communication with electronic controller 22. In the presently illustrated embodiment, both exhaust evaluation device 81 and exhaust evaluation device 83 can be considered to be fluidly positioned in parallel with each other and with the exhaust evaluation device that includes the particulate measurement gravimetric filter 50. As examples, and for instance, exhaust evaluation device 81 could be a particulate sizer or counter, whereas exhaust evaluation device 83 might be a polyurethane foam cartridge for speciation. Devices 81 and 83 are considered parallel with gravimetric filter 50 due to the fact that only a portion of the diluted sample flow in conduit 48 reaches filter 50 since devices 81 and 83 either collect and save their relevant portions or vent the remnants of their portion of the diluted sample flow to atmosphere via another conduit section not shown.

The present disclosure also contemplates auxiliary exhaust evaluation devices 86 and/or 87 that are fluidly positioned in series with particulate measurement gravimetric filter 50. In particular, after the diluted sample flow passes through filter 50 and into conduit 49, a portion of that filtered diluted sample flow may be directed to exhaust evaluation device 86 via branch passage 72 and/or another sample portion be directed to exhaust evaluation device 87 via branch passage 73. In typical circumstances, only a portion of the filtered diluted sample flow will be directed into exhaust evaluation device 86 or 87, with the bulk being directed toward exit device 26. As with exhaust evaluation devices 81 and 83, exhaust evaluation devices 86 and 87 may or may not communicate with electronic controller 22 and may or may not include a separate mass flow controller depending upon the particular devices being utilized. For instance, exhaust evaluation device 86, which may be, for instance, a bag unit for obtaining and storing a gas sample for play back into a gaseous emissions analyzer post test. Thus, bag unit 86 may require a dedicated and separate mass flow controller 85 that communicates mass flow rate information too, and may receive mass flow rate commands from, electronic controller 22 via communication line 92. On the other hand, exhaust evaluation device 87 may itself be a gaseous emissions analyzer that includes an internal means known in the art for receiving a precise and known mass flow rate for analysis, but may communicate this information and/or be controlled in its operation via a communication line 93, connected to electronic controller 22.

Those skilled in the art will appreciate that any of the illustrated and non-illustrated communication lines 60-63 and/or 90-93 may be wireless. An auxiliary exhaust evaluation device according to the present disclosure may comprise any known and/or currently available systems including but not limited to particle sizers and/or counters, soot sizers and/or counters, specialized gravimetric filters, polyurethane foam cartridges for speciation, gaseous emissions analyzers, bag units, and any not yet known exhaust evaluation device that may become available in the future. As used in this disclosure, an exhaust evaluation device can be any device used for storing any portion of a diluted sample flow or for real time testing, examining or any way accessing any aspect of the exhaust flow originating from power source 30. The present disclosure provides a test apparatus 10 for simultaneously trapping particulate matter in a gravimetric filter 50 while also performing another unrelated test(s) via an auxiliary exhaust evaluation device or capturing a portion of diluted sampling flow for later testing. Thus, the same operating procedure for power source 30 may provide simultaneous sample for two or more different exhaust evaluation devices. Depending upon which branch passage 70-73 that the exhaust evaluation device is fluidly connected to, it may receive either gravimetrically filtered (devices 86 and 87) or unfiltered exhaust as in devices 81 and 83.

INDUSTRIAL APPLICABILITY

Adding auxiliary exhaust evaluation devices to known dilution systems creates additional problems that are not readily apparent. For instance, various flow rates in dilution system 20 must be precisely controlled in order to maintain flow velocity at the face of gravimetric filter 50 within the regulated range to obtain accurate results. In addition, because only a portion of the exhaust extracted by test probe 40 may reach gravimetric filter 50, the particulate matter measurement gained by filter 50 must be scaled to take into account any fraction of fluid flow that is diverted via branch passage 70 or 71 to an auxiliary exhaust evaluation device 81 or 83, respectively. In order to better illustrate these subtleties, FIG. 1 identifies several different flow rates $Q_x$ at different locations in dilution system 20, and the equations below help illustrate their various relationships.

$Q_1$=sampled exhaust flow rate
$Q_2$=diluent flow rate
$Q_3$=portion of diluted sampled flow rate directed to exhaust evaluation device 81
$Q_4$=diluted sample rate
$Q_5$=portion of diluted sample flow directed to particulate measurement gravimetric filter 50
$Q_6$=portion of filtered sample flow rate downstream from filter 50 that is directed toward exhaust evaluation device 87
$Q_7$=exit mass flow rate
Assumption=Devices 83 and 86 not used; valves 76 and 77 closed.

$$Q_1 = Q_7 + Q_3 + Q_6 - Q_2 \quad (1)$$

$$Q_4 = Q_1 + Q_2 = Q_3 + Q_6 + Q_7 \quad (2)$$

$$Q_5 = Q_4 - Q_3 = Q_6 + Q_7 \quad (3)$$

$$\text{Flow to Filter } 50 = Q_1(1 - (Q_3/(Q_3 + Q_6 + Q_7))) \quad (4)$$

$$Q_7 = Q_2 + Q_1 - Q_3 - Q_6 \quad (5)$$

$$\text{Dilution Ratio} = \frac{Q_3 + Q_6 + Q_7}{Q_1} \quad (6)$$

These equations provide a means by which the measurement of particulate matter trapped in the filter 50 may be scaled to take into account the mass flow rate $Q_3$ directed to device 81, for instance. Those skilled in the art will appreciate that the equations above assume that isolation valves 76 and 77 are closed so that no diluted exhaust flow reaches exhaust evaluation devices 83 and 86. Thus, those skilled in the art will appreciate that if those additional auxiliary devices were in use, additional $Q_x$ terms would be needed to balance the equations above to demonstrate a conservation of matter in dilution system 20.

Another subtle but important problem addressed by the present disclosure relates to the fact that flow velocity at the face of gravimetric filter 50 should be maintained at a certain level in order to achieve more accurate results. Similarly, it is important to maintain particulate residence time in the dilution system within a limited range, as partially determined by the volume of residence chamber 45, which may act as a primary or secondary diluter device (see e.g., U.S. Pat. No. 7,533,585). Thus, in order to accomplish this, the mass flow rate to auxiliary device 81 and/or 83 must be known precisely so that the mass flow rate $Q_5$ directed to gravimetric filter 50 is about the same as it would be in the case that no auxiliary device were included. The desired mass flow rate to filer 50 when no auxiliary exhaust evaluation devices are included can be considered for purposes of the present disclosure as a baseline flow rate. Thus, in order for $Q_5$ to correspond to a baseline flow rate, the diluent flow rate $Q_2$ must be increased over a baseline diluent flow rate in order to account for the portion of the diluted sample flow that is directed into branch passage 70 and/or 71 to exhaust evaluation device 81 and/or 83, respectively. As discussed earlier, the diluent flow rate $Q_2$ is controlled by diluent flow actuator 44 that receives commands, from electronic controller 22. Thus, in the case of exhaust evaluation device 83, there may be an assumption that it receives a known substantially fixed flow rate that may be entered manually into the logic associated with electronic controlled 22 so that controller 22 may command the diluent flow actuator 44 to allow a diluent flow equal to its baseline diluent flow plus the mass flow rate provided to exhaust evaluation device 83. Conversely, in the case of exhaust evaluation device 81, it may require instantaneous measurement of the flow rate it is receiving and communicate that information so that the diluent flow rate is continuously adjusted above the baseline diluent flow rate to account for a fluctuating mass flow rate being diverted to exhaust evaluation device 81 via branch passage 70. The flow rate $Q_3$ to exhaust evaluation device 81 may be fluctuating due to a desire to obtain different flow rates due to, for instance, transient operating conditions of power source 30, or due to uncertainties in the ability to mass flow controller 80 to precisely and accurately hold a fixed mass flow rate. In other words, the present system contemplates a strategy for accounting for small errors in desired mass flow rates to an auxiliary exhaust evaluation device and/or desired fluctuations in that mass flow rate, and to make near instantaneous correction in the diluent flow rate. This aspect helps to ensure that the portion of the diluted sample flow arriving at gravimetric filter 50 remains somewhat steady and the velocity of the face and the particle residence time within the volume of system 20 prior to the filter 50 of the filter can be held at or near a known and desired value.

Auxiliary exhaust evaluation devices 86 and 87 present different complications for dilution system 20 over and above those associated with exhaust evaluation devices 81 and 83 that are located upstream or in parallel with gravimetric filter 50. In particular, the baseline system operates by exit flow meter 54 being monitored to maintain a desired flow rate through the system which is controlled by commands to exit flow actuator 53. However, if an auxiliary exhaust evaluation device 86 or 87 is also in operation, electronic controller 22 must know the mass flow rate being diverted so that electronic controller 22 can accurately assess what exit flow meter 54 should see, and hence control exit flow actuator 53 to permit a mass flow rate equal to a baseline exit flow rate minus the diverted flow rate to the auxiliary exhaust evaluation device 86 and/or 87. Depending upon the particular exhaust evaluation device, its flow rate may be a known and fixed value that could be keyed in or entered manually and supplied to electronic controller 22 or may be monitored and continuously provided to electronic controller 22, such as via mass flow controller 85 shown in association with exhaust evaluation device 86. For example, if exhaust evaluation device 86 requires a fluctuating exhaust mass flow rate to correspond to a transient operating condition of power source 30, the electronic controller 22 can adjust mass flow controller 85 in an appropriate manner to meet the demands of device 86. In addition, that same information can be utilized to command changes in the a control of exit flow actuator 53 to take into account the instantaneous changes in mass flow rate $Q_7$ under a baseline exit flow rate associated with the system when no auxiliary devices are being utilized.

In the illustrated embodiment, if all of the exhaust evaluation devices 81, 83, 86 and 87 were operating simultaneously, the electronic controller 22 would be required to supplement a baseline diluent flow to account for the mass flow rates diverted into branch passages 70 and 71. In addition, the electronic controller 22 would be required to adjust down from a baseline exit flow rate at exit flow actuator 53 to account for the mass flow rates being diverted into branch passages 72 and 73. Those skilled in the art would appreciate that although the illustrated embodiment shows two branch passages 70 and 71 upstream from gravimetric filter 50 in two auxiliary branch passage 72 and 73 downstream from filter 50, the present disclosure contemplates any number of branch passages to accommodate any number of desired auxiliary exhaust evaluation devices. Nevertheless, those skilled in the art will appreciate that the operating logic in electronic controller 22 might need to be adjusted to account for whatever number of exhaust evaluation devices and their respective steady state or fluctuating flow rates occur during a testing procedure in order to obtain accurate results. In addition, the present disclosure also contemplates operating test apparatus 10 in the case where no measurement of particulate matter in filter 50 occurs and that the system is operated only with auxiliary exhaust evaluation devices. In such a case, exit device 26 may be shut off and closed all together or it may provide for some exit flow to facilitate the proper operation of the auxiliary exhaust evaluation devices.

Because the illustrated test apparatus can respond to changes produced in the exhaust stream by power source 30 to change the mass flow rates within dilution system 20, the test apparatus 10 is particularly well suited to evaluating exhaust from a power source operating in a transient mode. For purposes of the present disclosure, those exhaust evaluation devices such as device 83 and 87 that supposedly have a known mass flow rate, those known mass flow rates may be characterized as estimates, although those estimated flow rates may be extremely accurate. Conversely, the mass flow rates to exhaust evaluation devices 81 and 86 may be considered to be measured mass flow rates due to the inclusion of respective mass flow controllers 80 and 85 that communicate mass flow rate information to electronic controller 22 as previously described. Thus, those skilled in the art will appreciate that if only a fixed mass flow rate exhaust evaluation device 83 were in operation, the diluent flow rate could merely be set at a level corresponding to a baseline diluent flow rate plus the estimated flow rate to exhaust evaluation device 83. In addition, if only a fixed mass flow rate device 87 were used downstream from filter 50, the exit flow rate could be set at a baseline exit flow rate minus the estimated flow rate being diverted into exhaust evaluation device 87. On the other hand, in cases where the diverted sample flow is measured, such as by mass flow controller 80, the diluent flow rate may be continuously adjusted responsive to that measured diverted flow rate to exhaust evaluation device 81. Likewise, if the downstream exhaust evaluation device 85 has a potentially fluctuating flow, that diverted flow rate can be measured such as by mass flow controller 85, and that information may be utilized to continuously adjust the exit flow rate below a baseline exit flow rate via appropriate control of exit flow actuator 53.

The present disclosure provides a test apparatus and strategy for simultaneously evaluating various different aspects of exhaust, such as particulate matter and gaseous emissions measurements simultaneously, even while power source 30 is being operated in a transient mode. Also, the dilution system of the present disclosure has greater flexibility and range over that associated with full dilution systems which can require as much or more than 1000 times the mass flow rate associated with dilution system 20 of the present disclosure. Thus, the test apparatus 10 may permit evaluation of exhaust from engines far larger than those that can be accommodated with any currently known full dilution systems. Test apparatus 10 also has the flexibility of being able to accurately evaluate exhaust from small engines as well. Test apparatus 10 also allows for two or more exhaust evaluation procedures to occur without the necessity of two complete dilution systems. Finally, with relatively minor adjustments to the control logic associate with electronic controller 22, flexibility is provided to utilize the same test apparatus 10 with one, two or more different evaluation devices working simultaneously and still able to achieve accurate results with all of the various devices.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A method of operating a dilution system, comprising the steps of:
    extracting a sample flow from an exhaust stream of a power source;
    adding diluent to the sample flow to produce a diluted sample flow;
    dividing the diluted sample flow into a first portion flow and a second portion flow;
    directing the first portion flow to a first exhaust evaluation device;
    directing the second portion flow to a second exhaust evaluation device;
    estimating at least one of a first portion flow rate and a second portion flow rate, to produce an estimate; and
    setting one of a dilution flow rate and an exit flow rate responsive to the estimate.

2. The method of claim 1 including a step measuring at least one of the first portion flow rate and the second portion flow rate; and
    the setting step includes adjusting one of the dilution flow rate and the exit flow rate responsive to the measurement during a test of the power source.

3. The method of claim 1 including a step of operating the power source in a transient mode during the extracting step.

4. The method of claim 1 including a step of trapping particles in the first portion flow in a particulate measurement gravimetric filter.

5. The method of claim 4 wherein the dividing step is performed upstream from the particulate measurement gravimetric filter.

6. The method of claim 5 including a step of dividing the second portion flow downstream of the particulate measurement gravimetric filter; and
directing part of the divided second portion flow to a third exhaust evaluation device.

7. The method of claim 6 including a step of estimating a second portion flow rate, to produce an upstream auxiliary estimate;
setting a dilution flow rate responsive to the upstream auxiliary estimate;
estimating a divided second portion flow rate, to produce a downstream auxiliary estimate; and
setting an exit flow rate responsive to the downstream auxiliary estimate.

8. The method of claim 7 including a step measuring the second portion flow rate, to produce an upstream auxiliary measurement;
the dilution flow setting step includes adjusting the dilution flow rate responsive to the upstream auxiliary measurement during a test of the power source;
measuring a divided second portion flow rate, to produce a downstream auxiliary measurement; and
the exit flow setting step includes adjusting the exit flow rate responsive to the downstream auxiliary measurement.

9. The method of claim 4 wherein the dividing step is performed downstream from the particulate measurement gravimetric filter.

10. The method of claim 9 including a step of measuring gaseous emissions in the second portion flow.

11. The method of claim 4 including the steps of:
estimating at least one of a first portion flow rate and a second portion flow rate, to produce an estimate; and
scaling a measurement of particles trapped in the particulate measurement gravimetric filter responsive to the estimate.

12. A test apparatus comprising:
a test probe sized for opening into an exhaust line for receiving exhaust sample flow originating from a power source;
a dilution device with a dilution flow actuator for adding diluent to the sample flow to produce a diluted sample flow;
a first exhaust evaluation device fluidly positioned to receive a first portion of the diluted sample flow;
a second exhaust evaluation device fluidly positioned to receive a second portion of the diluted sample flow;
an exit device that includes a vacuum pump and an exit flow actuator, and being fluidly positioned to receive at least part of the diluted sample flow;
wherein the first exhaust evaluation device and the second exhaust evaluation device are arranged in parallel relative to the diluted sample flow;
wherein the first exhaust evaluation device includes a particulate measurement gravimetric filter; and
an electronic controller configured to set the diluent flow actuator to increase diluent flow over a baseline diluent flow commensurate with a second portion flow rate.

13. The test apparatus of claim 12 including a flow meter in communication with the electronic controller and fluidly positioned to measure the second portion flow rate; and
the electronic controller is configured to adjust the diluent flow actuator responsive to the measured second portion flow rate during a transient test of a power source.

14. The test apparatus of claim 12 wherein the first exhaust evaluation device and the second exhaust evaluation device are arranged in series relative to the diluted sample flow.

15. The test apparatus of claim 14 wherein the first exhaust evaluation device includes a particulate measurement gravimetric filter; and
an electronic controller configured to set the exit flow actuator to decrease exit flow relative to a baseline exit flow commensurate with a second portion flow rate.

16. The test apparatus of claim 15 including a flow meter in communication with the electronic controller and fluidly positioned to measure the second portion flow rate; and
the electronic controller is configured to adjust the exit flow actuator responsive to the measured second portion flow rate during a transient test of the power source.

17. A test apparatus comprising:
a power source fluidly connected to an exhaust line;
a test probe that opens into the exhaust line for receiving exhaust sample flow originating from the power source;
a dilution device with a dilution flow actuator for adding diluent to the sample flow to produce a diluted sample flow;
a first exhaust evaluation device that includes a particulate measurement gravimetric filter fluidly positioned to receive a first portion of the diluted sample flow;
a second exhaust evaluation device fluidly positioned to receive a second portion of the diluted sample flow, and the second exhaust evaluation device is one of a particle sizer, a particle counter, a soot sizer, a soot counter, a specialized gravimetric filter, a polyurethane foam cartridge, a gaseous emissions analyzer, a bag storage unit and a different sampling device;
an exit device that includes a vacuum pump and an exit flow actuator, and being fluidly positioned to receive at least part of the diluted sample flow;
an electronic controller configured to set the dilution flow actuator to increase diluent flow over a baseline diluent flow commensurate with a second portion flow rate.

* * * * *